US012728079B2

(12) United States Patent
Wen et al.

(10) Patent No.: US 12,728,079 B2
(45) Date of Patent: Sep. 8, 2026

(54) POWDER DISPERSION COMPOSITION AND COSMETIC OBTAINED USING SAME

(71) Applicant: Shiseido Company, Ltd., Tokyo (JP)

(72) Inventors: Chunming Wen, Tokyo (JP); Ryushi Fukuhara, Tokyo (JP); Kuanting Lin, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 503 days.

(21) Appl. No.: 18/266,680

(22) PCT Filed: Jan. 7, 2022

(86) PCT No.: PCT/JP2022/000316

§ 371 (c)(1),
(2) Date: Jun. 12, 2023

(87) PCT Pub. No.: WO2022/153928

PCT Pub. Date: Jul. 21, 2022

(65) Prior Publication Data

US 2024/0041709 A1 Feb. 8, 2024

(30) Foreign Application Priority Data

Jan. 12, 2021 (JP) ............................ JP2021-002737

(51) Int. Cl.
*A61K 8/02* (2006.01)
*A61K 8/06* (2006.01)
*A61K 8/92* (2006.01)
*A61Q 17/04* (2006.01)

(52) U.S. Cl.
CPC ................ *A61K 8/022* (2013.01); *A61K 8/06* (2013.01); *A61K 8/92* (2013.01); *A61Q 17/04* (2013.01)

(58) Field of Classification Search
None
See application file for complete search history.

(56) References Cited

U.S. PATENT DOCUMENTS

2017/0216187 A1 8/2017 Toyoshima et al.

FOREIGN PATENT DOCUMENTS

| | | | |
|---|---|---|---|
| JP | 2013-121940 A | | 6/2013 |
| JP | 2013121940 | * | 6/2013 |
| JP | 2018-203633 A | | 12/2018 |
| JP | 2019-112384 A | | 7/2019 |
| JP | 2019-151605 A | | 9/2019 |
| WO | WO-2016/080270 A1 | | 5/2016 |

* cited by examiner

*Primary Examiner* — Nannette Holloman
(74) *Attorney, Agent, or Firm* — Foley & Lardner LLP

(57) ABSTRACT

An objective of the present invention is to provide a powder dispersion composition provided with high powder dispersibility, and a cosmetic having excellent properties in use and good stability over time due to using the powder dispersion composition. The powder dispersion composition according to the present invention contains (A) a powder, (B) an oil component, and (C) polyglyceryl polyricinoleate, wherein the (B) oil component contains (b1) a polar oil and (b2) a volatile oil; the (b1)) polar oil constitutes 35% to 80% by mass of the overall amount of the (B) oil component; the (b2) volatile oil is 20% by mass or more volatile hydrocarbon oil; and the (C) polyglyceryl polyricinoleate constitutes 0.5% to 10% by mass relative to the overall amount of the powder dispersion composition.

6 Claims, No Drawings

POWDER DISPERSION COMPOSITION AND COSMETIC OBTAINED USING SAME

CROSS-REFERENCE TO RELATED APPLICATIONS

This application is the U.S. National Stage of PCT/JP2022/000316, filed Jan. 7, 2022, which claims priority to JP 2021-002737, filed Jan. 12, 2021.

TECHNICAL FIELD

The present invention relates to a powder dispersion composition provided with high powder dispersibility, and to a cosmetic using the same and having excellent properties in use and good stability over time.

BACKGROUND ART

Although pigments, represented by titanium oxide, zinc oxide, iron oxide, etc., and powders, such as mica and sericite, are widely used in cosmetics, they are highly aggregative and are difficult to keep stable over time in cosmetics. Thus, various studies have been performed for dispersing them uniformly in products.

For example, Patent Document 1 discloses an oil-based dispersion composition in which a polyglycerin-modified silicone and/or an alkyl/polyglycerin-comodified silicone is used as a dispersant for uniformly dispersing a powder, and a cosmetic containing the oil-based dispersion composition.

Additionally, Patent Document 2 and Patent Document 3 disclose powder dispersion compositions in which a powder dispersant comprising a specific polyglycerin fatty acid ester is used to disperse a powder in an oil, and cosmetics containing the powder dispersion compositions.

However, in the case in which both a volatile oil and a polar oil are present as oil components, the powders tend to aggregate and become difficult to adequately disperse. Additionally, on the other hand, when a large amount of a dispersant is blended in order to avoid aggregation of the powder, there are cases in which stickiness occurs and the properties in use are degraded. In particular, the problems tend to become pronounced when the proportion of silicone oil in the volatile oil is high.

Therefore, a powder dispersion composition that can stably disperse a powder even when both a volatile oil and a polar oil are present as oil components, and furthermore, that does not become sticky when used in a cosmetic and that has excellent properties in use is still sought.

RELATED ART

Patent Documents

Patent Document 1: JP 2012-012302 A
Patent Document 2: WO 2016/080270
Patent Document 3: JP 2013-121940 A

SUMMARY OF THE INVENTION

Problem to be Solved by the Invention

The present invention was made in consideration of the aforementioned circumstances, and an objective of the invention is to provide a powder dispersion composition provided with high powder dispersibility, and a cosmetic having excellent properties in use and good stability over time due to using the powder dispersion composition.

Means for Solving the Problem

The present inventors performed diligent research towards solving the above-mentioned problem, as a result of which they discovered that a powder dispersion composition that exhibits high dispersibility, that does not tend to become sticky, and that has excellent properties in use can be realized by using polyglyceryl polyricinoleate as a dispersant, and by also adjusting the ratio of polar oils contained in the oil component and the ratio of volatile hydrocarbon oils in the volatile oil to be within prescribed ranges.

That is, the present invention is a powder dispersion composition containing (A) a powder, (B) an oil component, and (C) polyglyceryl polyricinoleate, wherein:

the (B) oil component contains (b1) a polar oil and (b2) a volatile oil;

the (b1) polar oil constitutes 35% to 80% by mass of the overall amount of the (B) oil component;

the (b2) volatile oil is 20% by mass or more volatile hydrocarbon oil; and the (C) polyglyceryl polyricinoleate constitutes 0.5% to 10% by mass relative to the overall amount of the powder dispersion composition. The present invention also is a cosmetic using said powder dispersion composition.

Effects of the Invention

The powder dispersion composition according to the present invention, by having the above-mentioned features, can provide high powder dispersibility despite containing both a volatile oil and a polar oil in the oil component. In addition thereto, since there is no need to blend a large quantity of a dispersant, stickiness does not occur and the properties in use are not degraded.

Additionally, the cosmetic using this powder dispersion composition has good stability over time and can also realize excellent properties in use.

MODES FOR CARRYING OUT THE INVENTION

The powder dispersion composition of the present invention is characterized by containing, on the basis of a prescribed blending ratio, (A) a powder, (B) an oil component, and (C) polyglyceryl polyricinoleate, wherein the (B) oil component has a prescribed composition. The present invention will be explained in detail below.

<(A) Powder>

The (A) powder is not particularly limited as long as it is a powder component that is commonly used in cosmetics or the like. Powder components include, for example, inorganic powders such as talc, kaolin, mica, silica and zeolite; organic powders such as polyamide resin powders (nylon powders), polyethylene powders, polymethyl methacrylate powders, polystyrene powders, styrene-acrylic acid copolymer resin powders, polytetrafluoroethylene powders and cellulose powders; silicone powders such as trimethyl silsequioxane powder; inorganic white pigments such as titanium dioxide and zinc oxide; inorganic red pigments such as iron oxide (red iron oxide); inorganic yellow pigments such as yellow iron oxide and ocher; inorganic black pigments such as black iron oxide and carbon black; inorganic green pigments such as chromium oxide, chromium hydroxide and cobalt titanate; inorganic blue pigments such as ultramarine blue and Prussian blue; pearlescent pigments such as titanium oxide-coated mica, colored titanium oxide-coated mica, bismuth oxychloride and argentine; metal powder pigments such as aluminum powder and copper powder; organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401 and Blue No. 404, and zirconium, barium or aluminum lakes such as Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3 and Blue No. 1; and powders obtained by treating the above. Treatment agents include, but are not limited to, silicones, fluoride compounds, higher fatty acids, etc.

Additionally, in order to provide UV protection effects, a powder (UV scattering agent) that physically blocks UV rays by reflection or scattering may be contained as the (A) powder. Specific examples of UV scattering agents include titanium oxide, zinc oxide, cerium oxide, barium sulfate, iron oxide, talc, mica, sericite, kaolin, titanated mica, Prussian blue, chromium oxide, chromium hydroxide, silica, cerium oxide, etc.

The lower limit of the blended amount of the (A) powder in the powder dispersion composition of the present invention is 5% by mass or more, more preferably 10% by mass or more, and particularly preferably 15% by mass or more relative to the overall amount of the powder dispersion composition. Additionally, the upper limit of the blended amount of the (A) powder is 50% by mass or less, more preferably 40% by mass or less, and particularly preferably 30% by mass or less. If the blended amount of the (A) powder is less than 5% by mass, then there are cases in which the effects that are due to blending the powder cannot be sufficiently obtained, and if more than 50% by mass is blended, then there are cases in which the dispersibility and the feel in use become poor.

<(B) Oil Component>

The (B) oil component refers to all types of oil components used in cosmetics, such that (b1) a polar oil and (b2) a volatile oil are essentially included as part of the (B) oil component. Hereinafter, the (b1) polar oil, the (b2) volatile oil, and other oil components will be explained in order.

<(b1) Polar Oil>

The (b1) polar oil preferably has an IOB value within the range 0.1 to 0.8, and more preferably has an IOB value within the range 0.15 to 0.6.

The IOB value in this case is the ratio (Inorganic Organic Balance) of the inorganic value (IV) with respect to the organic value (OV) in an organic conceptual diagram, which is referred to as "inorganic value (IV)/organic value (OV)".

Organic conceptual diagrams were proposed by Atsushi Fujita, and are explained in detail in *Pharmaceutical Bulletin*, vol. 2, 2, pp. 163-173 (1954); *Kagaku no ryoiki* [*Journal of Japanese Chemistry*], vol. 11, 10, pp. 719-725 (1957); *Fragrance Journal*, vol. 50, pp. 79-82 (1981), etc. That is, the fundamental source of all organic compounds is considered to be methane ($CH_4$), and all other compounds are viewed as derivatives of methane. Certain numerical values are set, respectively, for the number of carbon atoms, the substituent groups, the types of bonds (differences between single bonds, double bonds and triple bonds), rings, etc. The scores are summed to determine organic values and inorganic values, which are plotted on a diagram with the organic value on the X axis and the inorganic value on the Y axis. Organic conceptual diagrams are also described in *Yuki Gainenzu—Kiso to Oyo*—[*Organic Conceptual Diagrams—Fundamentals and Applications*] (by Yoshio Koda, Sankyo Shuppan, 1984), etc.

Typical examples of the (b1) polar oil include ester oils, oil-soluble UV absorbing agents, and ether oils.

Specific examples of ester oils include, but are not limited to, diisopropyl sebacate, pentaerythrityl tetraethylhexanoate, cetyl ethyl hexanoate, di(phytosteryl/octyldodecyl) lauroyl glutamate, triisostearin, glyceryl diisostearate, triethylhexanoin, ethylhexyl isononanoate, ethylhexyl ethylhexanoate, ethylhexyl salicylate, propylene glycol dicaprate, isopropyl palmitate, phytosteryl macadamiate, polygyceryl-2 tetraisostearate, ethylhexyl palmitate, myristyl myristate, isopropyl myristate, octyldodecyl myristate, decyl oleate, isodecyl neopentanoate, alkyl (C12-15) benzoate, tripropylene glycol dineopentanoate, etc.

Additionally, oil-soluble UV absorbing agents include, for example, methoxycinnamic acid derivatives, salicylic acid derivatives, benzoyl derivatives, camphor derivatives, para-aminobenzoic acid derivatives, triazine derivatives, benzophenone derivatives, and polysilicone-based UV absorbing agents. More specifically, examples include 2-ethylhexyl para-methoxycinnamate, oxybenzone, 4-t-butyl-4'-methoxydibenzoylmethane, octyl triazone, bis-ethylhexyloxyphenol methoxyphenyl triazine, dioctyl butamido triazone, diethylamino hydroxybenzoyl hexyl benzoate, octocrylene, polysilicone-15, octyl salicylate, homomenthyl salicylate, p-methylbenzylidene camphor, etc.

Furthermore, the ether oils are preferably polyoxyalkylene-based ether oils, for example, polypropylene glycol, polyoxypropylene butyl ether, etc.

The blended amount of the (b1) polar oil in the powder dispersion composition according to the present invention is 35% to 80% by mass relative to the overall amount of the (B) oil component. The lower limit is 35% by mass or more, more preferably 50% by mass or more, and particularly preferably 60% by mass or more. The upper limit is 80% by mass or less, more preferably 75% by mass or less, and particularly preferably 70% by mass or less. If the blended amount of the (b1) polar oil is less than 35% by mass of the overall amount of the (B) oil component, then there are cases in which a smooth texture in use cannot be obtained, and if the blended amount exceeds 80% by mass, then there are cases in which stickiness occurs and the spreadability becomes poor.

<(b2) Volatile Oil>

The (b2) volatile oil refers to an oil component having a boiling point within the range from 60 to 260° C. at ambient pressure (1 atm). Examples of the volatile oil used in the present invention include volatile hydrocarbon oils, silicone oils, etc., among which a volatile hydrocarbon oil is essentially contained.

As the volatile hydrocarbon oil, either a linear type or a branched type may be used. Specific examples include C8-C16 isoalkanes (also known as isoparaffins) such as isodecane, isododecane, isohexadecane, hydrogenated polyisobutene, etc.

Additionally, volatile silicone oils include, for example, cyclic polysiloxanes such as octamethyl cyclotetrasiloxane, decamethyl cyclopentasiloxane, dodecamethyl cyclohexasiloxane and tetramethyl tetrahydrogen cyclotetrasiloxane; linear polysiloxanes such as dimethyl polysiloxane, methylphenyl polysiloxane and methylhydrogen polysiloxane, or caprylyl methicone, etc.

The blended amount of the (b2) volatile oil in the powder dispersion composition according to the present invention is preferably 20% by mass or more, more preferably 25% by mass or more, and most preferably 30% by mass or more relative to the overall amount of the (B) oil component. Additionally, the blended amount is preferably 65% by mass or less, more preferably 60% by mass or less, and most preferably 50% by mass or less.

The blended amount of the volatile hydrocarbon oil in the (b2) volatile oil is 20% by mass or more, more preferably 30% by mass or more, and particularly preferably 50% by mass or more. The upper limit of the blended amount, though not particularly limited, is preferably 90% by mass or less, more preferably 80% by mass or less, and particularly preferably 70% by mass or less. If the blended amount of the volatile hydrocarbon oil is less than 20% by mass of the overall amount of the (b2) volatile oil, there is a tendency for the powder dispersibility to be poor.

<Other Oil Components>

The (B) oil components are not particularly limited aside from the (b1) polar oil and the (b2) volatile oil, but may include, for example, a non-volatile hydrocarbon oil such as squalane, hydrogenated polydecene or vaseline, a non-volatile silicone oil, such as dimethyl polysiloxane or methylphenyl polysiloxane, that is liquid at room temperature (25° C.).

The lower limit of the blended amount of the (B) oil component in the powder dispersion composition of the present invention is 55% by mass or more, more preferably 60% by mass or more, and particularly preferably 70% by mass or more relative to the overall amount of the powder dispersion composition. If the blended amount of the (B) oil component is less than 55% by mass, then there are cases in which sufficient stability cannot be obtained. Additionally, the upper limit of the blended amount of the (B) oil component, though not particularly limited, is preferably 95% by mass or less, more preferably 90% by mass or less, and particularly preferably 85% by mass or less.

<(C) Polyglyceryl Polyricinoleate>

The (C) polyglyceryl polyricinoleate blended into the powder dispersion composition of the present invention is an ester, with a polyglycerin having an average degree of polymerization of 2 to 10, of a condensate (condensed ricinoleic acid) obtained by ester-bonding ricinoleic acid, which is a higher fatty acid having 18 carbon atoms. A typical example is polyglyceryl-6 polyricinoleate.

The (C) component may be a commercially available product, and preferable commercial products include, for example, NIKKOL Decaglyn PR-20 (Nikko Chemicals Co., Ltd.), and SY Glyster CR-310, CR-500 and CRS-75 (all Sakamoto Yakuhin Kogyo Co., Ltd.).

The blended amount of the component (C) in the powder dispersion composition of the present invention is 0.5% to 10% by mass relative to the overall amount of the powder dispersion composition. The lower limit is 0.5% by mass or more, more preferably 2% by mass or more, and particularly preferably 3% by mass or more. The upper limit is 10% by mass or less, more preferably 6% by mass or less, and particularly preferably 4% by mass or less. If the blended amount of component (C) is less than 0.5% by mass, then the powder dispersibility tends to become poor. Additionally, if the blended amount of the component (C) exceeds 10% by mass, when the powder dispersion cosmetic is used as a cosmetic, there are cases in which stickiness occurs, the cosmetic becomes difficult to spread and the properties in use are degraded.

<Arbitrary Blended Components>

The powder dispersion composition of the present invention is mainly an oil-based dispersion in which a powder is dispersed in an oil, and may contain, in addition to the above-mentioned components (A) to (C), various types of components that are normally blended into oil-based cosmetics, such as gelling agents, antioxidants and preservatives, within a range not compromising the effects of the present invention, in accordance with the purpose.

The method for manufacturing the powder dispersion composition of the present invention is not particularly limited, but may, for example, involve mixing component (B) and component (C), adding component (A) thereto, and uniformly dispersing the components. At this time, the equipment used for uniform dispersion may be a dispersion mixer, a homo-mixer, a ball mill, a beads mill, etc.

<Cosmetic>

The powder dispersion composition of the present invention can be used, unmodified, as an oil-based cosmetic. Additionally, it may be emulsified with water phase components by means of a known method, and used as an emulsion cosmetic containing the powder dispersion composition as an oil phase.

The cosmetic of the present invention is the above-mentioned powder dispersion composition itself, or is obtained by blending the powder dispersion composition, and thus has excellent powder dispersibility and properties in use.

Components that are normally used in cosmetics, for example, water, alcohols, water-soluble polymers, surfactants, fragrances, salts, antioxidants, pH adjusters, chelating agents, colorants, cosmetic components, etc. may be added to the cosmetic of the present invention within a range not compromising the effects of the present invention.

Aside from sunscreen cosmetics, the cosmetic of the present invention can be widely applied to makeup products, hair-care products, etc.

EXAMPLES

The present invention will be explained in further detail by providing examples below. However, the present invention is not limited in any way by these examples. Where not particularly noted otherwise, the blended amounts are expressed in percentage by mass relative to the systems in which those components are blended.

Example 1 and Comparative Examples 1 to 7

Various dispersants were used to prepare the powder dispersion compositions having the compositions indicated in Table 1 below, and the powder dispersibilities were analyzed by means of the method described below.

TABLE 1

| | Comp. Ex. 1 | Comp. Ex. 2 | Comp. Ex. 3 | Comp. Ex. 4 | Comp. Ex. 5 | Comp. Ex. 6 | Comp. Ex. 7 | Ex. 1 |
|---|---|---|---|---|---|---|---|---|
| Isododecane (b2) | 17.2 | 17.2 | 17.2 | 17.2 | 17.2 | 17.2 | 17.2 | 17.2 |
| Polypropylene glycol (b1) | 1.7 | 1.7 | 1.7 | 1.7 | 1.7 | 1.7 | 1.7 | 1.7 |
| Isopropyl myristate (b1) | 5.2 | 5.2 | 5.2 | 5.2 | 5.2 | 5.2 | 5.2 | 5.2 |

TABLE 1-continued

| | Comp. Ex. 1 | Comp. Ex. 2 | Comp. Ex. 3 | Comp. Ex. 4 | Comp. Ex. 5 | Comp. Ex. 6 | Comp. Ex. 7 | Ex. 1 |
|---|---|---|---|---|---|---|---|---|
| Diisopropyl sebacate (b1) | 17.2 | 17.2 | 17.2 | 17.2 | 17.2 | 17.2 | 17.2 | 17.2 |
| Alkyl (C12-15) benzoate (b1) | 6.4 | 6.4 | 6.4 | 6.4 | 6.4 | 6.4 | 6.4 | 6.4 |
| Tripropylene glycol dineopentanoate (b1) | 3.4 | 3.4 | 3.4 | 3.4 | 3.4 | 3.4 | 3.4 | 3.4 |
| Octocrylene (b1) | 8.6 | 8.6 | 8.6 | 8.6 | 8.6 | 8.6 | 8.6 | 8.6 |
| Polysilicone-15 (b1) | 1.7 | 1.7 | 1.7 | 1.7 | 1.7 | 1.7 | 1.7 | 1.7 |
| bis-Ethylhexyloxyphenol methoxyphenyl triazine (b1) | 0.9 | 0.9 | 0.9 | 0.9 | 0.9 | 0.9 | 0.9 | 0.9 |
| Diethylamino hydroxybenzoyl hexyl benzoate (b1) | 3.4 | 3.4 | 3.4 | 3.4 | 3.4 | 3.4 | 3.4 | 3.4 |
| Octyl salicylate (b1) | 8.6 | 8.6 | 8.6 | 8.6 | 8.6 | 8.6 | 8.6 | 8.6 |
| Polyglyceryl-2 diisostearate *[1] | 3.4 | — | — | — | — | — | — | — |
| Sorbitan sesquiisostearate *[2] | — | 3.4 | — | — | — | — | — | — |
| bis-Butyldimethicone polyglyceryl-3 *[3] | — | — | 3.4 | — | — | — | — | — |
| Polyglyceryl-10 (isostearate/succinate) *[4] | — | — | — | 3.4 | — | — | — | — |
| Cetyl dimethicone copolyol *[5] | — | — | — | — | 3.4 | — | — | — |
| PEG-10 dimethicone *[6] | — | — | — | — | — | 3.4 | — | — |
| Amodimethicone *[7] | — | — | — | — | — | — | 3.4 | — |
| Polyglyceryl-6 polyricinoleate *[8] | — | — | — | — | — | — | — | 3.4 |
| Titanium oxide | 3.4 | 3.4 | 3.4 | 3.4 | 3.4 | 3.4 | 3.4 | 3.4 |
| Zinc oxide | 18.9 | 18.9 | 18.9 | 18.9 | 18.9 | 18.9 | 18.9 | 18.9 |
| Total | 100 | 100 | 100 | 100 | 100 | 100 | 100 | 100 |
| Powder dispersibility | D | D | D | D | D | D | C | A |

*[1] "WOGEL-18DV", Matsumoto Pharmaceutical Co., Ltd.
*[2] "Estemol 182V", Nisshin Oillio Group
*[3] "KF-6109", Shin-Etsu Chemical Co., Ltd.
*[4] "S-Face SCIS-101", Sakamoto Yakuhin Kogyo Co., Ltd.
*[5] "ABIL EM90", Evonik
*[6] "Silicon SC9450N", Shin-Etsu Chemical Co., Ltd.
*[7] "KF-8004", Shin-Etsu Chemical Co., Ltd.
*[8] "SY Glister CRS-75", Sakamoto Yakuhin Kogyo Co., Ltd.

<Powder Dispersibility>

Each of the powder dispersion compositions that were prepared was placed in a sample feeder in a stress-controlled rheometer (manufactured by Aton Paar) and a cone-plate tool CP50-1 was used to measure the shear stress at shear rates from 0.1 $S^{-1}$ to 1000 $S^{-1}$. The shear viscosity was determined by using the expression below:

[Shear viscosity]=[Shear stress]/[Shear rate]

A flow curve representing the relationship between the shear viscosity and the shear rate was obtained. In the resulting flow curve, the viscosity values η(10/S) and η(1000/S) at 10 $S^{-1}$ and 1000 $S^{-1}$ were used to calculate the viscosity attenuation rate from the expression below:

[Mathematical Expression 1]

$$[\text{Viscosity attenuation rate}] = \frac{\eta(10/S) - \eta(1000/S)}{\eta(10/S)}$$

The smaller the value of the viscosity attenuation rate, the lower the degree of viscosity change associated with increases in the shear rate, and the dispersibility of the powder can be evaluated to be higher. The calculated viscosity attenuation rates were used to determine the powder dispersibilities using the criteria below.

A: Viscosity attenuation rate equal to or lower than 0.2

B: Viscosity attenuation rate higher than 0.2 and equal to or lower than 0.4

C: Viscosity attenuation rate higher than 0.4 and equal to or lower than 0.7

D: Viscosity attenuation rate higher than 0.7

As indicated in Table 1, the powder dispersibility was confirmed to be particularly excellent when polyglyceryl-6 polyricinoleate was blended, compared with various types of dispersants that are widely used in cosmetics.

Examples 2 to 4 and Comparative Examples 8 and 9

Powder dispersion compositions having the compositions indicated in Table 2 below were prepared by changing the blending ratios of polyglycelyl-6 polyricinoleate, and the powder dispersibilities were evaluated.

Additionally, the properties in use were also analyzed by the method below.

<Properties in Use>

Each of the prepared powder dispersion compositions was evaluated for the properties in use (smoothness, lack of squeakiness) when applied to skin, by the method below.

Twenty panelists who were cosmetic evaluation experts used the powder dispersion compositions and performed a five-level evaluation of the properties in use in accordance with the criteria below, and each powder dispersion composition was scored. Furthermore, the average score of all of the panelists was assessed in accordance with the four-level assessment criteria below.

| (Evaluation criteria) | |
|---|---|
| Evaluation result | Score |
| Very good | 5 |
| Good | 4 |
| Fair | 3 |
| Slightly poor | 2 |
| Poor | 1 |

| (Assessment criteria) | |
|---|---|
| Assessment | Average score |
| A | 4.5 or higher |
| B | 3.5 or higher, lower than 4.5 |
| C | 1.5 or higher, lower than 3.5 |
| D | lower than 1.5 |

TABLE 2

| | Comp. Ex. 8 | Comp. Ex. 9 | Ex. 2 | Ex. 3 | Ex. 4 |
|---|---|---|---|---|---|
| Isododecane (b2) | 17.8 | 17.7 | 17.6 | 17.2 | 16.3 |
| Polypropylene glycol (b1) | 1.8 | 1.8 | 1.8 | 1.7 | 1.6 |
| Isopropyl myristate (b1) | 5.3 | 5.3 | 5.3 | 5.2 | 4.9 |
| Diisopropyl sebacate (b1) | 17.8 | 17.7 | 17.6 | 17.2 | 16.3 |
| Alkyl (C12-15) benzoate (b1) | 6.6 | 6.6 | 6.5 | 6.4 | 6.0 |
| Tripropylene glycol dineopentanoate (b1) | 3.6 | 3.5 | 3.5 | 3.4 | 3.3 |
| Octocrylene (b1) | 8.9 | 8.9 | 8.8 | 8.6 | 8.2 |
| Polysilicone-15 (b1) | 1.8 | 1.8 | 1.8 | 1.7 | 1.6 |
| bis-Ethylhexyloxyphenol methoxyphenyl triazine (b1) | 0.9 | 0.9 | 0.9 | 0.9 | 0.8 |
| Diethylamino hydroxybenzoyl hexyl benzoate (b1) | 3.6 | 3.5 | 3.5 | 3.4 | 3.3 |
| Octyl salicylate (b1) | 8.9 | 8.9 | 8.8 | 8.6 | 8.2 |
| Polyglyceryl-6 polyricinoleate *8 | 0.0 | 0.4 | 0.9 | 3.4 | 8.2 |
| Titanium oxide | 3.5 | 3.5 | 3.5 | 3.4 | 3.3 |
| Zinc oxide | 19.5 | 19.5 | 19.5 | 18.9 | 18.0 |
| Total | 100 | 100 | 100 | 100 | 100 |
| Powder dispersibility | D | D | B | A | A |
| Properties in use | D | C | B | A | B |

As indicated in Table 2, it was confirmed that the powder dispersibility was excellent when 0.5% by mass or more of polyglyceryl-6 polyricinoleate was blended.

Meanwhile, though not indicated in the table, when more than 10% by mass of polyglyceryl-6 polyricinoleate was blended, the powder dispersibility was good, but stickiness occurred and poor results were obtained in terms of the properties in use.

Examples 5 to 9 and Comparative Examples 10 to 16

The powder dispersion compositions having the compositions indicated in Table 3 and Table 4 below were prepared by changing the blending ratios of the volatile hydrocarbon oil (isododecane), the volatile silicone oil (dimethyl polysiloxane) and the polar oil (isopropyl myristate) in the oil component, and the powder dispersibilities and properties in use were analyzed in the same manner as that described above.

TABLE 3

| | Ex. 5 | Ex. 6 | Ex. 7 | Ex. 8 | Comp. Ex. 10 | Comp. Ex. 11 |
|---|---|---|---|---|---|---|
| Isododecane (b2) | 16.5 | 32.9 | 16.5 | 8.2 | 16.5 | 0.0 |
| Dimethyl polysiloxane (1.5 cs) (b2) | 16.5 | 16.5 | 32.9 | 24.7 | 49.3 | 16.5 |
| Isopropyl myristate (b1) | 49.3 | 32.9 | 32.9 | 49.4 | 16.5 | 65.8 |
| Polyglyceryl-6 polyricinoleate *8 | 2.4 | 2.4 | 2.4 | 2.4 | 2.4 | 2.4 |
| Titanium oxide | 2.4 | 2.4 | 2.4 | 2.4 | 2.4 | 2.4 |
| Zinc oxide | 12.9 | 12.9 | 12.9 | 12.9 | 12.9 | 12.9 |
| Total | 100 | 100 | 100 | 100 | 100 | 100 |
| Polar oil/all oil components (%) | 60 | 40 | 40 | 60 | 20 | 80 |
| Volatile hydro-carbon oil/all volatile oils (%) | 50 | 67 | 33 | 25 | 25 | 0 |
| Powder dispersibility | B | B | B | B | D | D |
| Properties in use | A | A | B | A | D | D |

TABLE 4

| | Ex. 9 | Comp. Ex. 12 | Comp. Ex. 13 | Comp. Ex. 14 | Comp. Ex. 15 | Comp. Ex. 16 |
|---|---|---|---|---|---|---|
| Isododecane (b2) | 28.8 | 8.2 | 0.0 | 82.3 | 8.2 | 0.0 |
| Dimethyl polysiloxane (1.5 cs) (b2) | 12.4 | 65.9 | 0.0 | 0.0 | 49.4 | 82.3 |
| Isopropyl myristate (b1) | 41.1 | 8.2 | 82.3 | 0.0 | 24.7 | 0.0 |
| Polyglyceryl-6 polyricinoleate *8 | 2.4 | 2.4 | 2.4 | 2.4 | 2.4 | 2.4 |
| Titanium oxide | 2.4 | 2.4 | 2.4 | 2.4 | 2.4 | 2.4 |
| Zinc oxide | 12.9 | 12.9 | 12.9 | 12.9 | 12.9 | 12.9 |
| Total | 100 | 100 | 100 | 100 | 100 | 100 |
| Polar oil/all oil components (%) | 50 | 10 | 100 | 0 | 30 | 0 |
| Volatile hydro-carbon oil/all volatile oils (%) | 70 | 11 | — | 100 | 14 | 0 |
| Powder dispersibility | B | D | C | C | D | D |
| Properties in use | A | D | D | B | D | D |

As indicated in Table 3 and Table 4, it was confirmed that excellent powder dispersibility and properties in use were obtained when the polar oil constituted 35% to 80% by mass of the overall amount of the oil component and the volatile oil is 20% by mass or more volatile hydrocarbon oil.

Meanwhile, it was observed that there is a tendency for the power dispersibility and the properties in use to become worse when either the blended amount of the polar oil in the oil component overall or the blended amount of the volatile hydrocarbon oil in the volatile oil is outside the above-mentioned ranges.

An example of the formulation of the cosmetic of the present invention is indicated below. Needless to say, the present invention is not limited in any way by this formulation example and is defined by the scope of the claims. The blended amounts all represent percentages by mass relative to the overall amount of the cosmetic.

Formulation Example 1: Sunscreen

| (Component name) | Blended amount (mass %) |
|---|---|
| (1) Isododecane | 10.0 |
| (2) Dimethyl polysiloxane (1.5 cs) | 15.0 |
| (3) Isopropyl myristate | 18.7 |
| (4) Octocrylene | 5.0 |
| (5) Ethylhexyl salicylate | 5.0 |
| (6) PEG-9 polydimethyl siloxyethyl dimethicone | 1.5 |
| (7) Polyglyceryl-6 polyricinoleate | 2.0 |
| (8) Disteardimonium hectorite | 0.3 |
| (9) Titanium oxide | 2.0 |
| (10) Zinc oxide | 11.0 |
| (11) Talc | 7.0 |
| (12) Purified water | balance |
| (13) EDTA-3Na | 0.1 |
| (14) Ethanol | 6.0 |
| (15) Glycerin | 1.0 |

The invention claimed is:

1. A powder dispersion composition containing (A) a powder, (B) an oil component, and (C) polyglyceryl polyricinoleate, wherein:

the (B) oil component contains (b1) a polar oil and (b2) a volatile oil;

the (b1) polar oil constitutes 50% to 80% by mass of the overall amount of the (B) oil component;

the (b2) volatile oil is 20% by mass or more of a volatile hydrocarbon oil, relative to the total mass of the (b2) volatile oil; and the (C) polyglyceryl polyricinoleate constitutes 0.5% to 10% by mass relative to the overall amount of the powder dispersion composition.

2. The powder dispersion composition according to claim 1, wherein the (b1) polar oil is selected from among oil-soluble UV absorbing agents, and ester oils having an IOB value of 0.1 to 0.8.

3. The powder dispersion composition according to claim 1, wherein the (b2) volatile oil contains a volatile silicone oil.

4. The powder dispersion composition according to claim 1, wherein the volatile hydrocarbon oil is of one or more types selected from among isododecane, isodecane, isohexadecane and hydrogenated polyisobutene.

5. A cosmetic consisting of the powder dispersion composition according to claim 1.

6. An emulsion cosmetic containing, as an oil phase, the powder dispersion composition according to claim 1.

* * * * *